US006942875B2

(12) United States Patent
Hedgpeth

(10) Patent No.: US 6,942,875 B2
(45) Date of Patent: *Sep. 13, 2005

(54) ADHESIVE TREATMENT FOR SKIN YEAST INFECTIONS

(75) Inventor: Daniel L. Hedgpeth, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 695 days.

This patent is subject to a terminal disclaimer.

(21) Appl. No.: 09/898,093

(22) Filed: Jul. 5, 2001

(65) Prior Publication Data

US 2003/0007948 A1 Jan. 9, 2003

(51) Int. Cl.$^7$ .......................... A61F 13/02; A61L 15/16
(52) U.S. Cl. ...................... 424/448; 424/443; 424/445; 424/446; 424/447; 424/449
(58) Field of Search .............................. 424/448, 443, 424/446, 447, 449, 444, 445, 400, 401, 78.03, 78.31, 78.07

(56) References Cited

U.S. PATENT DOCUMENTS

| | | | |
|---|---|---|---|
| 3,577,516 A | 5/1971 | Gould et al. |
| 3,847,155 A | 11/1974 | Bernaola |
| 3,880,158 A | 4/1975 | Gurney |
| 3,987,000 A | 10/1976 | Gleichenhagen et al. |
| 4,073,291 A | 2/1978 | Marvel et al. |
| 4,287,177 A | 9/1981 | Nakashima et al. |
| 4,310,509 A | 1/1982 | Berglund et al. |
| 4,323,557 A | 4/1982 | Rosso et al. |
| 4,479,933 A | 10/1984 | Akimova et al. |
| 4,560,555 A | 12/1985 | Snider |
| 4,643,180 A | 2/1987 | Feld et al. |
| 4,752,472 A | 6/1988 | Kligman |
| 4,806,614 A | 2/1989 | Matsuda et al. |
| 4,826,677 A | 5/1989 | Mueller et al. |
| 4,880,416 A | 11/1989 | Horiuchi et al. |
| 4,913,897 A | 4/1990 | Chvapil et al. |
| 4,981,483 A | 1/1991 | Akimova et al. |
| 4,987,893 A | 1/1991 | Salamone et al. |
| 5,009,224 A | 4/1991 | Cole |
| 5,082,663 A | 1/1992 | Konishi et al. |
| 5,103,812 A | 4/1992 | Salamone et al. |
| 5,160,737 A | 11/1992 | Friedman et al. |
| 5,254,132 A | 10/1993 | Barley et al. |
| 5,306,490 A | 4/1994 | Barley, Jr. |
| 5,320,838 A | 6/1994 | Woller |
| 5,403,591 A | 4/1995 | Tighe et al. |
| 5,409,903 A | 4/1995 | Polak et al. |
| 5,413,780 A | 5/1995 | Huprich |
| 5,480,935 A | 1/1996 | Greff et al. |
| 5,514,371 A | 5/1996 | Leung et al. |
| 5,514,372 A | 5/1996 | Leung et al. |
| 5,530,037 A | 6/1996 | McDonnell et al. |
| 5,554,365 A | 9/1996 | Byram et al. |
| 5,575,997 A | 11/1996 | Leung et al. |
| 5,580,565 A | 12/1996 | Tighe et al. |
| 5,582,834 A | 12/1996 | Leung et al. |
| 5,613,942 A | 3/1997 | Lucast et al. |
| 5,624,669 A | 4/1997 | Leung et al. |
| 5,653,769 A | 8/1997 | Barley, Jr. et al. |
| 5,661,170 A | 8/1997 | Chodosh |
| 5,665,817 A | 9/1997 | Greff et al. |
| 5,684,042 A | 11/1997 | Greff et al. |
| 5,716,607 A | 2/1998 | Byram et al. |
| 5,716,608 A | 2/1998 | Byram et al. |
| 5,717,005 A | 2/1998 | Richardson |
| 5,725,491 A | 3/1998 | Tipton et al. |
| 5,730,994 A | 3/1998 | Askill et al. |
| 5,753,699 A | 5/1998 | Greff et al. |
| 5,755,680 A | 5/1998 | Ghodsian |
| 5,762,919 A | 6/1998 | Greff et al. |
| 5,762,955 A | 6/1998 | Smith |
| 5,783,177 A | 7/1998 | Greff et al. |
| 5,800,373 A | 9/1998 | Melanson et al. |
| 5,800,831 A | 9/1998 | Burnett et al. |
| 5,807,563 A | 9/1998 | Askill et al. |
| 5,811,091 A | 9/1998 | Greff et al. |
| 5,811,107 A | 9/1998 | Gangadharan et al. |
| 5,827,870 A | 10/1998 | Chodosh |
| 5,840,072 A | 11/1998 | Carey |
| 5,855,208 A | 1/1999 | Askill et al. |
| 5,981,621 A | 11/1999 | Clark et al. |
| 6,001,345 A | 12/1999 | Askill et al. |
| 6,086,906 A | 7/2000 | Greff et al. |
| 6,090,397 A | 7/2000 | Lee et al. |
| 6,102,205 A | 8/2000 | Greff et al. |
| 6,155,265 A | 12/2000 | Hammerslag |
| 6,183,190 B1 | 2/2001 | Raiteri |
| 6,183,593 B1 | 2/2001 | Narang et al. |
| 6,238,692 B1 | 5/2001 | Smith |
| 6,433,096 B1 | 8/2002 | Hickey et al. |
| 6,585,967 B2 * | 7/2003 | Narang et al. ............ 424/78.31 |
| 6,602,496 B2 * | 8/2003 | Hedgpeth et al. ......... 424/78.07 |
| 6,746,667 B2 * | 6/2004 | Badejo et al. ............ 424/78.31 |
| 2001/0038857 A1 | 11/2001 | Smith |
| 2001/0051179 A1 | 12/2001 | Berman |

FOREIGN PATENT DOCUMENTS

| WO | WO 00/35276 | 6/2000 |
|---|---|---|
| WO | WO 01/32795 A1 | 5/2001 |

OTHER PUBLICATIONS

Iowa Department of Public Health, "Tinea Corporis", Jun. 1999.

* cited by examiner

Primary Examiner—Thurman K. Page
Assistant Examiner—Isis Ghali
(74) Attorney, Agent, or Firm—Hutchinson & Mason PLLC

(57) ABSTRACT

A method of treating or preventing skin yeast infections, such as cutaneous candidiasis, includes applying a polymerizable monomer adhesive composition to an area of skin afflicted with or susceptible to a skin yeast infection, optionally with at least one of an additional anti-fungal agent or a skin care additive, and allowing the polymerizable monomer composition to polymerize to form a polymer film over the area of skin.

36 Claims, No Drawings

ADHESIVE TREATMENT FOR SKIN YEAST INFECTIONS

BACKGROUND OF THE INVENTION

1. Field of Invention

The present invention relates to treatment and prevention of skin yeast infections such as cutaneous candidiasis.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

U.S. Pat. Nos. 5,514,371, 5,514,372, 5,575,997, 5,624,669, and 5,582,834 to Leung et al. disclose the addition of a therapeutic agent in a cyanoacrylate composition. The cyanoacrylate adhesive forms a matrix for the therapeutic agent, with the therapeutic agent being released in vivo over time from the matrix during biodegradation of the polymer.

U.S. Pat. No. 5,762,955 to Smith discloses a treatment for healthy, damaged, diseased, or infected biological tissue by applying a bioadhesive coating in conjunction with a medication. The treatment is directed, in part, to treating external biological tissue that may be affected by harmful afflictions such as bruises, burns, dermatological afflictions, infections, gashes, wounds, herpes sores, canker sores, or intra-oral lesions, and skin cancers such as leukemia. Smith further discloses several medications that may be used including corticosteroids, fluoroouracil, obtundants, anesthetics, antibiotics, fungicides, anti-inflammatory agents, antibacterial agents, antiseptic agents, and other medications or combinations of medications used in processes for healing tissue, promoting or preventing blood clotting, destroying cancer cells, palliative treatments and killing of bacteria or viruses.

U.S. Pat. No. 4,880,416 to Horiuchi et al., discloses a dermal bandage of a pre-formed film-like adhesive material for preventing dermally applied ointments, creams, solutions, powders, etc. from falling off, and for delivering drugs, such as anti-fungal agents, to affected parts of the skin. U.S. Pat. Nos. 5,716,607 and 5,716,608, both to Byram et al., disclose the use of cyanoacrylate adhesives to prevent ionization radiation damage to skin. Such damage is prevented by applying the cyanoacrylate polymer to the skin to be protected. U.S. Pat. No. 5,653,769 to Barkey, Jr., et al., discloses protecting skin areas from irritation due to contact with artificial devices such as prosthetics, bandages and casts by applying a cyanoacrylate polymer to the desired skin areas that otherwise would be prone to ulceration or irritation by the devices.

U.S. Pat. No. 4,287,177 to Nakashima et al. discloses a protective covering material for forming a film or coat on the skin or wound surface, wherein the film may contain an anti-fungal agent that is controllably released when the composition is placed in contact with the skin. U.S. Pat. Nos. 5,684,042; 5,753,699; 5,762,919; 5,783,177; and 5,811,091 to Greff et al. disclose a cyanoacrylate composition with a compatible anti-fungal agent to form an anti-fungal polymeric cyanoacrylate film to be applied on mammalian skin as wound dressings, wound bandages, surgical incise drapes, wound closure materials and the like.

Cutaneous candidiasis, also more commonly and generically referred to as skin yeast infection, is a yeast infection or dermatophytosis of the skin, generally caused by yeast species such as of *Candida* and *Blastomyces,* particularly or most commonly by the yeast species of *Candida albicans, Candida tropicalis*, and *Blastomyces dermatitidis*. The condition generally includes itching, which can be severe or intense, and skin lesions or rash, generally characterized by enlarging patches, macules or papules, reddened (such as beefy red) and/or raw patches of skin, and where the lesions or rash may also be scaly or have satellite blister-like or pimply-like lesions. The condition generally occurs on areas of skin that are warm and moist, such as around skin folds, in the genital or buttock areas, on the trunk, under the breasts, in the arm pits, and the like, but can occur and/or spread to other skin areas.

As used herein, the term "skin yeast infection" or like terms, unless specifically stated to the contrary, is intended to refer to such skin yeast infection as described above, caused by any yeast species not being limited to the *Candida* yeast. However, the term is not intended to refer to related yeast infections, such as vaginal yeast infections or oral-based yeast infections, such as that known as oral thrush or oral candidiasis. The term skin yeast infection thus also is not intended to refer to similar skin conditions, such as tinea that is caused by fungal infections.

Physicians commonly prescribe medications in the form of powders, aerosols, liquids or creams for the treatment of skin yeast infections. Such medications are also commonly obtained by individuals "over-the-counter" for treatment of the same skin condition. The source of the affliction can often be a matter of personal health and hygiene, can be related to other health conditions, and can be a public safety and health concern. For example, skin yeast infections can generally occur directly from the presence of the yeast on the body, particularly in dead skin and nails or in the warm, moist areas of the body. Skin yeast infections can also arise based on other bodily conditions. For example, skin yeast infections can be more prevalent in women during pregnancy, when the body is undergoing hormonal changes, or in patients with decreased immune system function, such as those with AIDS. From a public health and safety concern, the occurrence and transmission of skin yeast infections is higher in public areas such as locker rooms, public showers or pools, sports facilities, and the like, where direct contact with an infected individual or his or her clothing or other articles is increased.

As described above, often the condition occurs on the skin areas of the body that are warm and moist, such as around skin folds, in the genital or buttock areas, on the trunk, under the breasts, in the arm pits, and the like. These areas of skin typically are prone to higher levels of moisture, and also come into frequent frictional contact with a patient's clothing or with other skin surfaces. As a result of this frictional contact, as well as contact with clothing and the like, topically applied medications can be more easily removed from the affected areas of a patient's skin. Moreover, the topically applied medications are more prone to the affects of moisture that is present at the affected area of skin. These difficulties mean that treatment is significantly reduced, because the medication is not held in place for a sufficient time. As a result, the efficacy of the treatment is significantly reduced, and patients must frequently reapply medications so that the affected area receives proper treatment. Furthermore, the inconvenience of bandages due to constant or frequent movement and flexing of the skin, the small surface area usually involved, friction and moisture, make bandages impractical for minimizing frictional contact that occurs at the affected areas of a patient's skin, as well as impractical as a means to hold the medication in place for longer periods of time.

In addition, conventional treatment regimens for skin yeast infections continue to pose significant public health and safety concerns. Because conventional treatments have the above-described problems of being easily removed from the afflicted skin and being susceptible to moisture, there is a much greater chance that the skin yeast infection can be spread. This spread of the yeast can be either to other parts of the same patient's body, or to other individuals such as through direct contact with the individual, direct contact with the individuals clothing or other articles, or even indirectly through other means such as shower and pool surfaces or the like.

Despite the known use of adhesives, such as described above, such adhesives have not been used in the treatment of skin yeast infections. Instead, the majority of skin yeast infection treatments currently on the market include topically applied medications that have the problems of being easily removed from the application site, being prone to moisture effects, and resulting in higher spread or transmission rates. Therefore, there is a need for an alternative skin yeast infection treatment that remains at the application site for longer periods, that reduces the spread or transmission of the skin yeast infection, and that provides fast, effective relief from the symptoms of skin yeast infection.

SUMMARY OF THE INVENTION

The present invention provides methods for preventing and/or treating skin yeast infection by applying a monomeric adhesive composition to the affected area, or to areas that are prone to infection. The monomeric adhesive composition of the present invention preferably comprises a polymerizable 1,1-disubstituted ethylene monomer such as a cyanoacrylate monomer, that may include or be accompanied by an additional anti-fungal agent. The composition reduces moisture contact with the affected skin area, keeps any active ingredients in contact with the affected skin area for a longer time, provides fast and effective treatment of skin yeast infection, and can act to prevent infection in the first instance, or prevent the spread of an infection to other areas.

The present invention provides an unexpected treatment or prevention composition and method for skin yeast infections, because polymerizable monomers such as 1,1-disubstitutyed ethylene monomers and cyanoacrylates have not previously been used to treat or prevent such skin conditions. Moreover, while such polymerizable monomers have been variously used on other parts of the body, such as for sealing open wounds, their use for treating or preventing skin yeast infections, on areas of skin such as around skin folds, in the genital or buttock areas, on the trunk, under the breasts, in the arm pits, and the like and surrounding areas, is an entirely and new and unexpected use of the materials.

The present treatment for or prevention of skin yeast infection is advantageous for several reasons. First, because a skin yeast infection affects the skin in areas that are warm and moist, and often fully clothed, as well as surrounding areas, it is often very difficult for the patient to keep a treatment agent in contact with the affected skin area for an extended period of time. This is either because frictional contact with the affected area tends to disturb any applied active agents, or because higher levels of moisture present in the area tend to affect or likewise disturb the applied agent. Furthermore, because the treatment and prevention methods of the present invention provide a stronger physical barrier at the affected skin area, the risks of spread or transmission of the skin yeast infection, either to other areas of the patient's body or to other individuals, is significantly decreased. The present invention thus provides significant public health benefits.

Because cyanoacrylates tend to polymerize rapidly to form a relatively robust polymerized film, cyanoacrylates applied to an affected area of a patient's skin (or to an area prone or susceptible to infection) can provide fast, effective protection over the affected area and other skin surfaces. By protecting the affected area from moisture and frictional contact, the cyanoacrylate compound can hold any applied active agents in place for a longer period of time and can accordingly significantly increase the time of exposure of an applied medication to the affected area, ensure more effective treatment, and minimize the possibility of re-infection or transmission of the skin yeast infection to other areas of the patient's body or to other individuals. Likewise, the same benefits can be obtained by applying the composition of the present invention to an area prone or susceptible to infection, which in turn aids in preventing spread or transmission of the infection.

In addition to forming a stronger barrier to keep moisture away from the affected area while maintaining active agents in contact with the area, cyanoacrylate compounds are also desirable for the treatment or prevention of skin yeast infections because of their inherent anti-fungal properties. In laboratory tests, it has been discovered that at least some cyanoacrylate compounds or formulations, even in the absence of an added anti-fungal agent, appears to inhibit skin yeast infections. Because of this anti-fungal property, such cyanoacrylate compounds and formulations may be especially desirable for treating or preventing skin yeast infections, even without the introduction or pre-application of other anti-fungal agents. Moreover, the anti-fungal properties of such cyanoacrylate compounds and formulations may also be beneficial in instances where an anti-fungal agent is applied before, or together with, the cyanoacrylate, because the cyanoacrylate can continue to provide its anti-fungal effect even after the applied anti-fungal agent has been completely absorbed or used up.

In addition, cyanoacrylate compounds are also useful as anti-fungal agent carriers or delivery agents. In this capacity, the cyanoacrylate compound provides the same protective and anti-fungal benefits, but also offers the added benefit of enhancing the treatment of the affected area by controllably releasing an anti-fungal agent to the affected area, or providing prolonged preventative benefits to an applied area by controllably releasing an anti-fungal agent to the area.

The present invention also provides various applicators that are suitable for applying the adhesive composition.

DETAILED DESCRIPTION OF PREFERRED EMBODIMENTS

This invention is directed to methods of treating skin yeast infection in general, or cutaneous candidiasis in particular, by applying a monomeric adhesive composition to an afflicted area of a patient's skin, such as areas of skin that are warm and moist, such as around skin folds, in the genital or buttock areas, on the trunk, under the breasts, in the arm pits, and the like. This invention is also directed to methods of preventing skin yeast infection in general, or cutaneous candidiasis in particular, by applying a monomeric adhesive composition to an area of a patient's skin that is prone or susceptible to such infection.

According to embodiments of the present invention, the adhesive composition can be applied alone, or it can be applied subsequent to or concurrent with the application of a separate anti-fungal agent. Furthermore, in embodiments, the cyanoacrylate composition can itself include an anti-fungal agent in addition to polymerizable monomer.

According to the present invention, "treat" (or other forms of the word such as "treating" and "treatment") refers to employment of the methods against an established yeast infection. "Treat" thus encompasses both amelioration of effects of the yeast infection, such as by reducing swelling, irritation, pain and the like, and active reduction of the infection such as by killing the yeast and preventing re-growth of the yeast at an infected area.

According to the present invention, "prevent" (or other forms of the word such as "preventing" and "prevention") refers to employment of the methods against a subsequent fungal infection, such as at areas of skin that are prone or susceptible to fungal infection. "Prevent" thus encompasses both prevention of spread of an established fungal infection, as well as prevention of infection in the first instance on the particular patient.

In embodiments of the invention, an adhesive composition can be used alone for treating or preventing skin yeast infections. In such embodiments, a patient or care-provider simply applies the composition to an area of the skin, such as areas of skin that are warm and moist, such as around skin folds, in the genital or buttock areas, on the trunk, under the breasts, in the arm pits, and the like, afflicted with a skin yeast infection, or to an area where prevention of infection is desired. The composition then is permitted to polymerize to form a robust polymeric coating that effectively covers and protects the affected or applied area of the patient's skin. Anti-fungal properties of the composition may inhibit or kill microbes, and the robust polymeric coating that the composition forms protects the area from frictional contact with clothing or other skin surfaces so that prolonged treatment or prevention can be achieved.

Preferably, the composition is applied in a sufficient amount to entirely cover the desired area, which generally would correspond to an affected area where a skin yeast infection is present, or to an area that is prone or susceptible to skin yeast infection. In embodiments, the composition covers an additional area around the desired area, for example to prevent further infection.

According to the present invention, the adhesive composition is preferably permitted to substantially or fully polymerize to form a polymer film before the treated area is permitted to contact other surfaces. Thus, for example, when the composition is applied to areas of skin such as around skin folds, in the genital or buttock areas, on the trunk, under the breasts, and in the arm pits, the respective skin areas are preferably kept separated from each other until the composition has substantially or fully polymerized, to prevent bonding the skin areas together.

In further embodiments of the present invention, the adhesive composition can be applied over a medicament for treating or preventing skin yeast infections. The medicament in this embodiment is not particularly limited, and can include any of the available medicaments for the skin condition. The medicament can also be, or comprise, any suitable anti-fungal agent, as described below. In this embodiment, the medicament can be first applied to the affected or desired area, followed by application of a polymerizable adhesive composition. The medicament can be in any suitable form, including liquid, solid, powder, cream or the like, and can include only a medicament or can include other suitable additives such as diluents, carriers or the like. Where the medicament is in a liquid or a semi-liquid form, it is preferred that the medicament be permitted to dry, substantially or completely, prior to application of the adhesive composition. However, the adhesive composition can also be immediately applied over the applied medicament, or can be applied prior to drying of the medicament, if desired.

In embodiments of the present invention, an appropriate, preferably monomer-compatible, anti-fungal agent can be mixed with the polymerizable adhesive composition and a resultant composition applied to the affected or desired area. In this embodiment, the anti-fungal agent can be mixed with the polymerizable adhesive composition during manufacture (i.e. prior to packaging the materials), or immediately prior to use. However, the present invention is not limited to such embodiments. Thus, for example, the anti-fungal agent need not be monomer-compatible. In these embodiments, the anti-fungal agent can be mixed or combined with the polymerizable adhesive composition, usually just prior to application, and a resultant composition applied to the affected or desired area In further embodiments of the present invention the anti-fungal agent may also serve as a polymerization initiator or a stabilizer. Thus, the anti-fungal agent can provide not only a biological activity, but a chemical one as well.

Anti-fungal agents that also serve as polymerization initiators can initiate and/or accelerate the polymerization of the composition when applied to an affected or desired area of skin. Accelerated polymerization reduces the waiting time necessary after application, and makes the composition more convenient to apply. Suitable anti-fungal agents that can also serve as initiators include, but are not limited to, certain acidic and quaternary ammonium compounds. In embodiments where the anti-fungal agent also acts as a polymerization initiator or rate modifier, the present invention provides the additional advantage of not requiring that a further, separate polymerization initiator or rate modifier be used. Furthermore, in these embodiments, the anti-fungal agent is preferably located in a non-contacting relationship with the adhesive composition prior to use, so that premature polymerization of the adhesive composition does not occur.

Anti-fungal agents that also serve as stabilizers can extend the useful life of the composition. By increasing the useful life of the composition, the composition can be stored and packaged for longer periods of time without the risk of premature polymerization. Suitable anti-fungal agents that can also serve as stabilizers can include, but are not limited to, certain acidic and phenolic compounds. In embodiments where the anti-fungal agent also acts as a stabilizer for the adhesive composition, the present invention provides the additional advantage of not requiring that a further, separate stabilizer be used. Furthermore, in these embodiments, the anti-fungal agent is preferably located in a contacting relationship with the adhesive composition, such as being mixed with the adhesive composition, prior to use.

Although a mixture of anti-fungal agent and cyanoacrylate, according to the present invention, is not limited to a specific ratio of anti-fungal agent to cyanoacrylate, the anti-fungal agent is preferably present in an effective amount, preferably a therapeutically effective amount for treating or preventing the skin yeast infection.

When mixed or combined immediately prior to use, the anti-fungal agent can be mixed with the polymerizable cyanoacrylate composition in a suitable container and thereafter applied. Alternatively, mixing can be conducted during the application process, for example by using an applicator that is loaded with anti-fungal agent, which thereby mixes the agent with the adhesive composition during application.

Suitable anti-fungal agents include, but are not limited to, known agents such as parabens, cresols, azoles, allylamines, pollyenes, acidics, mercurials, quaternary ammonium compounds, other agents, non-polymer-stabilized compounds, i.e., that are not complexed with or otherwise part of a polymer species, mixtures thereof, and the like. Such anti-fungal agents should preferably be present in a therapeutically effective amount, particularly in cases where higher amounts may otherwise be toxic to the patient.

For example, suitable parabens include, but are not limited to, alkyl parabens and salts thereof, such as methylparaben, methylparaben sodium, ethylparaben, propylparaben, propylparaben sodium, butylparaben, and the like. Butyl-paraben is especially preferred as it can also act as a stabilizer for certain polymerizable monomers, such as cyanoacrylate monomers, in the adhesive composition. Suitable cresols include, but are not limited to, cresol, chlorocresol, and the like. Suitable azoles include, but are not limited to, voriconazole, ketoconazole, fluconazole, itraconazole, miconazole, clotrimazole, saperconazole, neticonazole, oxiconazole, isoconazole, sulconazole, tercanazole, tioconazole, and the like. Suitable allylamines include, but are not limited to, naftifine, SF86-327, and the like. Suitable polyenes include, but are not limited to, nyastatin, amphotericin B, pimaricin, and the like. Suitable acidics include, but are not limited to, benzoic acid and salts thereof, sorbic acid and salts thereof, propionic acids and salts thereof, boric acid and salts thereof, dehydroacetic acid, sulphurous and vanillic acids, and alkyl esters of pararhydrobenzoic acid. Suitable mercurials include but are not limited to, thiomersal, phenylmercuric acetate and nitrate, nitromersol and sodium ethylmercurithiosalicylate. Suitable quaternary ammonium compounds include, but are not limited to, benzalkonium chloride, cetylpyridinium chloride, benzethonium chloride, and cetyltrimethyl ammonium bromide. Other known agents that can be used include, but are not limited to, hydroquinone, pyrocatechol, resorcinol, 4-n-hexyl resorcinol, captan (i.e., 3a,4,7,7a-tetrahydro-2-((trichloromethyl)thio)-1H-isoindole1,3(2H)-dione), benzalkonium chloride, benzalkonium chloride solution, benzethonium chloride, benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, chlorothymol, alcohols, chlorobutanol, phenoxy-2-ethanol, benzyl alcohol, β-phenylethyl alcohol, chlorhexidine, 6-acetoxy-2,4-dimethyl-m-dioxane 2,4,4' trichloro-2'-hydroxy-diphenylether, imidizoldinylether urea compound, bromo-2-nitropropanediol-1,3 5-bromo-5-nitrol-1,3 dioxane 2-methyl 1-4-isothiazolin-3-one and 5 chloro derivative 1-(3-chloroallyl)-3,5,7-triazo 1-azoniaadamantane chloride (Dowicil 200), phenylmercuric compounds such as phenylmercuric borate, phenylmercuric nitrate and phenylmercuric acetate, formaldehyde, formaldehyde generators such as the preservatives Germall II® and Germall 115® (imidazolidinyl urea, available from Sutton Laboratories, Charthan, N.J.), morpholines, salicylic and benzoic acids, sodium and potassium iodides, flucytosine, 5-flucytosine, griseofulvin, terbinafine, cidofovir, famicoclovir, valacyclovir, echinocandins, pneumocandins, pradimicins, benanomicins, nikkomycins, amorolfine, polyoxins, duanorubicin citrate, doxorubicin hydrocholride, tolnaftate, ciclopirox, butenafine, and ergestrol biosynthesis inhibitors.

Non-polymer-stabilized compounds, i.e., that are not complexed with or otherwise part of a polymer species, which can be either soluble or insoluble in the monomeric composition, can also be used. Where the compounds are insoluble in the monomeric composition, they must generally be capable of releasing species, such as ions, which are soluble in the monomer composition and provide the anti-fungal effect. Thus such compounds either themselves are, or provide, the anti-fungal agent. Such suitable non-polymer-complexed materials include, but are not limited to, metals and metal compounds. Examples of such metal compounds or elemental metals include, but not limited to, mercurial compounds, such as phenolmercuric chloride, phenolmercuric acetate, acetomeroctol, nitromersol, thimerosal, mercurochrome, mercuric chloride, and mercuric iodide; elemental metals, such as silver and copper; and metal compounds, such as copper chloride, copper sulfate, copper peptides, zinc chloride, zinc sulfate, zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, silver nitrate, silver iodide, silver acetate, silver benzoate, silver carbonate, silver chloride, silver citrate, silver oxide, silver sulfate, and tincture of iodine; as well as mixtures thereof and the like. Copper peptides are discussed, for example, in "Copper: An Essential Element for Life," ProCyte Corporation, available at http://www.humatech.com/technology.html (Oct. 28, 1999), the entire disclosure of which is incorporated herein by reference. Further information on anti-fungal activities of metals can be found, for example, in S. Seymour Block, *Disinfection, Sterilization and Preservation*, 3$^{rd}$ *Ed.*, Philadelphia:Lea & Febiger, 1983, the entire disclosure of which is incorporated herein by reference. The ions from the metal, which constitute the anti-fungal agent, diffuse into and through the adhesive composition.

Other suitable anti-fungal agents include the various compounds identified as such in *The Merck Index*, 12$^{th}$ Ed. (1996), incorporated herein by reference. Such agents include acrisorein, 3-amino-4-hydroxybutyric acid, ammonium mercuric chloride, amorolfine, amphotericin B, anthralin, azaserine, benzoic acid, bifonazole, biphenamine, boric acid, bromosalicylchloranilide, buclosamide, butenafine, butoconazole, calcium propionate, candicidin, chlordantoin, chlormidazole, chlorphenesin, chlorquinaldol, ciclopirox, cloconazole, clotrimazole, cloxyquin, coparaffinate, m-cresyl acetate, cupric sulfate, dermostatin, diamthazole dihydrochloride, econazole, enilconazole, etisazol, exalamide, fenticonazole, filipin, fluconazole, flucytosine, flutrimazole, fungichromin, griseofulvin, hachimycin, halethazole, hamycin, hexetidine, isoconazole, itraconazole, ketoconazole, lanoconazole, loflucarban, lucensomycin, Magenta I, mepartricin, 2-(methoxymethyl)-5-nitrofuran, miconazole, monensin, myxin, naftifine, natamycin, neomycin undecylenate, nifuratel, nystatin, oligomycins, omoconazole, ontianil, oxiconazole nitrate, pecilocin, perimycin, phenylmurcuric nitrate (basic), potassium iodide, propionic acid, pyrithione, pyrrolnitrin, rubijervine, salicylanilide, salicylic acid, saperconazole, sertaconzole, siccanin, sodium propionate, sulbentine, sulconazole, tenonitrozole, terbinafine, terconazole, thimerosal, tioconazole, tolciclate, tolindate, tolnaftate, triacetin, 2,4,6-tribromo-m-cresol, tubercidin, ujothion, undecylenic acid, viridin, zinc propionate, mixtures thereof, and the like.

In embodiments of the present invention, the monomer composition can also be applied in conjunction with one or more conventional skin care additives. Suitable skin care additives that are typically used in the treatment of skin yeast infections and that can be applied in place of or in conjunction with the monomer composition and/or the anti-fungal agent of the present invention include, but are not limited to, miconazole nitrate, povidone iodine complex, cliquinol, haloprogin, tolnaftate and undecylenic acid, mixtures thereof, and the like.

In addition, in embodiments where monomer additives including, but not limited to those listed above, are insoluble with the monomer composition, the additive can be applied to a skin area before applying the monomer composition. In such embodiments, the additive and the monomer composition can be provided, for example, in separate packages in a kit.

In other embodiments, where such additives are soluble with the monomer composition, the additives can be combined with the monomer composition during manufacture of the composition. Moreover, in cases where the additive is soluble with the monomer composition, the additive can be applied before the monomer composition is applied, it can be pre-mixed with and applied together with the monomer composition, it can be mixed together with the monomer composition immediately before application, or it can even be applied after the monomer composition has been applied. As a result, in cases where a soluble additive is to be applied, the additive and the composition can be provided in a kit where the additive and the monomer composition are pre-mixed, or the additive and the monomer composition can be provided separately to be applied separately or mixed together immediately prior to, during, or after application.

Although a mixture of additive and cyanoacrylate, according to the present invention is not limited to a specific ratio of additive to cyanoacrylate, the additive is preferably present in an effective amount, and preferably in a therapeutically effective amount.

When mixed immediately prior to use, the additive can be mixed with the polymerized cyanoacrylate composition in a suitable container and thereafter applied. Alternatively, mixing can be conducted during the application process, for example by using an applicator loaded with skin care additive, which thereby mixes the additive with the adhesive composition during application.

In addition, as discussed above with respect to suitable anti-fungal agents, various skin care additives may also serve as polymerization initiators or rate modifiers. Also, suitable skin care additives may serve as stabilizers for the adhesive composition.

In embodiments, the monomer composition and/or its packaging can be sterilized. However, sterilization is by no means required, particularly in view of the fact that most commercially available products for the treatment of skin yeast infections are not sterilized. Furthermore, whether or not the composition and container is sterilized, the composition can further include one or more suitable preservative, as described below.

Sterilization of the monomer composition and/or its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. Pat. No. 6,143,805, the entire disclosure of which is incorporated herein by reference. The composition should also show low levels of toxicity to living tissue during its useful life. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

The monomer (including prepolymeric) adhesive composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687 and 5,928,611, to Leung et al., U.S. patent application Ser. No. 09/430,177, filed on Oct. 29, 1999, and U.S. Pat. No. 6,183,593, which are hereby incorporated in their entirety by reference herein.

The α-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane and others as listed in U.S. Pat. No. 6,183,593, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. Nos. 4,720,513, and 6,310,166, the disclosures of which are hereby incorporated in their entireties by reference herein.

The composition may optionally also include thickeners. Suitable thickeners may include poly (2-ethylhexyl methacrylate), poly(2-ethylhexyl acrylate) and others as listed in U.S. Pat. No. 6,183,593, the disclosure of which is incorporated by reference herein in its entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-fungal agents, such as, for example, various acidic anti-fungals, as identified above.

The stability, and thus the shelf-life, of some monomeric adhesive compositions can be further enhanced and extended through careful regulation of the packaging. Treated (e.g., fluorinated polymer) packaging such as that disclosed in copending U.S. patent application Ser. No. 09/430,289, filed Oct. 29, 1999, which is hereby incorporated by reference herein in its entirety, is preferred and may reduce the amount of stabilizer that is combined into the composition. As mentioned above, certain stabilizers including, but not limited to, certain acidics can also function as anti-fungal agents. In this case, the amount of the anti-fungal/stabilizer material is either not reduced below a level to provide the desired anti-fungal effect, or a further anti-fungal/non-stabilizing agent is added to ensure that the desired anti-fungal effect is provided.

The compositions may also include pH modifiers to control the rate of degradation of the resulting polymer, as disclosed in U.S. Pat. No. 6,143,352, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. Pat. No. 6,579,469, the entire disclosure of which is incorporated her in by reference. Such preservatives can be in addition to any anti-fungal agent that may or may not be added to the composition, as described above. Such preservatives can be irrespective of whether the composition and containers are sterilized.

In embodiments of the present invention, the composition and/or its applicator may contain materials such as a polymerization initiator, accelerator, rate-modifier, and/or cross-linking agent for initiating polymerization and/or cross-linking of the polymerizable monomer material. Suitable materials and applicators and packaging systems are disclosed in U.S. Pat. Nos. 5,928,611, 6,455,064, 6,595,940, 6,579,469, and 6,352,704 and U.S. patent applications Ser. Nos. 09/430,177, and 09/430,289, filed Oct. 29, 1999; Ser. No. 09/385,030, filed Aug. 30, 1999; and Ser. No. 09/176,889 filed Oct. 22, 1998; the entire disclosures of which are incorporated herein by reference.

According to the present invention, any suitable applicator can be used to apply the composition to the affected areas of skin. Suitable applicators and packaging systems are disclosed in, for example, U.S. Pat. Nos. 5,928,611, 6,455,064, 6,595,940, 6,579,469, and 6,352,704 and U.S. patent applications Ser. Nos. 09/430,177, and 09/430,289, filed Oct. 29, 1999; Ser. No. 09/385,030 filed Aug. 30, 1999; and Ser. No. 09/176,889 filed Oct. 22, 1998; the entire disclosures of which are incorporated herein by reference. A further suitable application is described in U.S. Pat. No. 6,746,667, the entire disclosures of which are incorporated herein by reference.

EXAMPLES

Example 1

A 2-octyl cyanoacrylate monomer composition is prepared by adding 30 mg of haloprogin, an anti-fungal agent, to 2 mL of 2-octyl cyanoacrylate monomer. The mixture is sealed in a glass vial and stirred.

The characteristics of the composition are observed at about one minute after preparation and later at least twenty-four hours after preparation. The results of the observations show that the solution remains clear, indicating that haloprogin is soluble in the monomer and does not cause premature polymerization.

The composition is then applied to an affected area of skin showing the characteristics of a skin yeast infection. The monomer composition polymerizes in under one minute, resulting in a polymerized film of material covering the affected area. The polymerized film will remain in place for at least three days.

While the invention has been described with reference to preferred embodiments, the invention is not limited to the specific examples given, and other embodiments and modifications can be made by those skilled in the art without departing from the spirit and scope of the invention.

What is claimed is:

1. A method of treating a skin yeast infection, comprising:
   a) applying an adhesive composition comprising a polymerizable monomer to an area of skin that is afflicted with a skin yeast infection; and
   b) allowing said polymerizable monomer composition to polymerize to form a polymer film over said area of skin wherein said polymerizable monomer composition is an α-cyanoacrylate monomer.

2. The method of claim 1, wherein said method is for treating said skin yeast infection, and said area of skin is afflicted with said skin yeast infection.

3. The method of claim 1, wherein said polymerizable monomer composition comprises a 1,1-disubstituted ethylene monomer.

4. The method of claim 1, wherein said monomer composition comprises at least one member selected form the group consisting of ethyl cyanoacrylate, butyl cyanoacrylate, and 2-octyl cyanoacrylate.

5. The method of claim 1, further comprising combining at least one of an anti-fungal agent or a skin care additive with the polymerizable monomer composition on the area so that the at least one agent or additive serves as a polymerization initiator for said polymerizable monomer composition.

6. The method of claim 1, wherein said composition further comprises at least one stabilizing agent for said polymerizable monomer.

7. The method of claim 6, wherein said stabilizing agent is also at least one of an anti-fungal agent or a skin care additive.

8. The method of claim 1, wherein said composition comprises at least one plasticizer.

9. The method of claim 8, wherein the plasticizer is selected from the group consisting of tributyl citrate, acetyl tributyl citrate, polymethylmethacrylate, polydimethylsiloxane and hexadimethylsilazane.

10. The method of claim 1, wherein the composition further comprises at least one of an anti-fungal agent or a skin care additive.

11. The method of claim 10, wherein said method is for treating said skin yeast infection, and said area of skin is afflicted with said skin yeast infection.

12. The method of claim 10, wherein the composition further comprises said at least one anti-fungal agent and said at least one anti-fungal agent is selected from the group consisting of parabens, cresols, azoles, allylamines, pollyenes, acidics, mercurials, quaternary ammonium compounds, and non-polymer-stabilized compounds.

13. The method of claim 10, wherein the composition further comprises said at least one anti-fungal agent and said at least one anti-fungal agent is a paraben selected from the group consisting of alkyl parabens having an alkyl group of from 1–4 carbon atoms.

14. The method of claim 10, wherein the composition further comprises said at least one anti-fungal agent and said at least one anti-fungal agent is selected from the group consisting of methylparaben, methylparaben sodium, ethylparaben, propylparaben, propylparaben sodium, butylparaben, cresol, chlorocresol, voriconazole, ketoconazole, fluconazole, itraconazole, miconazole, clotrimazole, saperconazole, neticonazole, oxiconazole, isoconazole, sulconazole, tercanazole, tioconazole, naftifine, SF86-327, nyastatin, amphotericin B, pimaricin, benzoic acid and salts thereof, sorbic acid and salts thereof, propionic acids and salts thereof, boric acid and salts thereof, dehydroacetic acid, sulphurous and vanillic acids, alkyl esters of pararhydrobenzoic acid, thiomersal, phenylmercuric borate, phenylmercuric acetate and phenylmercuric nitrate, nitromersol, sodium ethylmercurithiosalicylate, benzalkonium chloride, cetylpyridinium chloride, benzethonium chloride, cetyltrimethyl animonium bromide, hydroquinone, pyrocatechol, resorcinol, 4-n-hexyl resorcinol, 3a,4,7,7a-tetrahydro-2-((trichloromethyl)thio)-1H-isoindole-1,3(2H)-dione, benzalkonium chloride, benzethonium chloride, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, chlorothymol, alcohols, chlorobutanol, phenoxy-2-ethanol, benzyl alcohol, β-phenylethyl alcohol, chlorhexidine, 6-acetoxy-2,4-dimethyl-m-dioxane 2,4,4' trichloro-2'-hydroxy-diphenylether, imidizoldinylether urea compound, bromo-2-nitropropanediol-1,3 5-bromo-5-nitrol-1,3 dioxane, 2-methyl 1-4-isothiazolin-3-one and 5 chloro derivative, 1-(3-chloroallyl)-3,5,7-triazo 1-azoniaadamantane chloride, formaldehyde, imidazolidinyl urea, morpholines, salicylic acids, sodium iodides and potassium iodides, flucytosine, 5-flucytosine, griseofulvin, terbinafine, cidofovir, famicoclovir, valacyclovir, echinocandins, pneumocandins, pradimicins, benanomicins, nikkomycins, amorolfine, polyoxins, duanorubicin citrate, doxorubicin hydrocholride, tolnaftate, cyclopirox, butenafine, ergestrol biosynthesis inhibitors, acrisorein, 3-amino-4-hydroxybutyric acid, ammonium mercuric chloride, amorolfine, anthralin, azaserine, bifonazole, biphenamine, bromosalicyichloranilide, buclosamide, butoconazole, calcium propionate, candicidin, chlordantoin, chlormidazole, chlorphenesin, chlorquinaldol, cloconazole, cloxyquin, coparaffinate, m-cresyl acetate, cupric sulfate, dermostatin, diamthazole dihydrochloride, econazole, enilconazole, etisazol, exalamide, fenticonazole, filipin, flutrimazole, fungichromin, hachimycin, halethazole, hamycin, hexetidine, lanoconazole, loflucarban, lucensomycin, Magenta I, mepartricin, 2-(methoxymethyl)-5-nitrofuran, monensin, myxin, natamycin, neomycin undecylenate, nifuratel, oligomycins, omoconazole, ontianil, pecilocin, perimycin, pyrithione, pyrrolnitrin, rubijervine, salicylanilide, sertaconzole, siccanin, sulbentine, tenonitrozole, tolciclate, tolindate, triacetin, 2,4,6-tribromo-m-cresol, tubercidin, ujothion, undecylenic acid, viridin, and zinc propionate.

15. The method of claim 10, wherein the composition further comprises said at least one anti-fungal agent and said at least one anti-fungal agent is selected from the group consisting of cresol, clotrimazole, tolnaftate, terbinafine and tioconazole.

16. The method of claim 10, wherein the composition further comprises said at least one anti-fungal agent and said at least one anti-fungal agent is selected from the group consisting of benzoic acid and salts thereof, sorbic acid and salts thereof, propionic acid and salts thereof, boric acid and salts thereof, dehydroacetic acid, sulphurous acids, vanillic acids, phenol, cresol, chlorocresol, o-phenylphenol, chlorothymol, parabens, alkyl esters of parahydroxybenzoic acid, methyl- p-hydroxybenzoates, ethyl-p-hydroxybenzoates, propyl- p-hydroxybenzoates, benzyl-p-hydroxybenzoates and butyl-p-hydroxybenzoates, thimersal, phenylmercuric acetate and phenylmercuric nitrate, nitromersol, sodium ethylmercurithiosalicylate, benzalkonium chloride, cetylpyridium chloride, benzethonium chloride, cetyltrimethyl ammonium bromide, chlorobutanol, phenoxy-2-ethanol, benzyl alcohol, β-phenylethyl alcohol, chlorohexidine, chloroform, 6-acetoxy-2,4-dimethyl-m-dioxane, 2,4,4' trichloro-2'-hydroxy-diphenylether, imidizolidinyl urea compound, bromo-2nitropropanediol-1,3,5-bromo-5-nitrol-1,3 dioxane, 2-methyl-4-isothiazolin-3-one and 5 chloro derivative, and 1-(3-chloroallyl)-3,5,7-triazo 1-azoniaadamantane chloride.

17. The method of claim 10, wherein the composition further comprises said at least one skin care additive and said at least one skin care additive is selected from the group consisting of miconazole nitrate, povidone iodine complex, cliquinol, haloprogin, tolnaftate and undecylenic acid and mixtures thereof.

18. The method of claim 10, wherein the at least one anti-fungal agent or skin care additive is mixed with the polymerizable monomer composition immediately prior to applying the polymerizable monomer composition to the area of skin.

19. The method of claim 10, wherein the at least one anti-fungal agent or skin care additive is mixed with the polymerizable monomer composition during manufacture of the polymerizable monomer composition.

20. The method of claim 10, wherein the composition further comprises said at least one anti-fungal agent and said anti-fungal agent is a phenolic antioxidant.

21. The method of claim 20, wherein said antioxidant is a stabilizing agent for said monomer.

22. The method of claim 10, wherein the composition further comprises said at least one anti-fungal agent and said anti-fungal agent is butylparaben.

23. The method of claim 1, wherein said composition has a Sterility Assurance Level (SAL) of $10^{-3}$–$10^{-6}$.

24. The method of claim 1, further comprising applying at least one of an anti-fungal agent or a skin care additive to the area of skin before applying the adhesive composition.

25. The method of claim 24, wherein said method is for treating said skin yeast infection, and said area of skin is afflicted with said skin yeast infection.

26. The method of claim 24, further comprising allowing the at least one applied anti-fungal agent or skin care additive to substantially dry before applying the adhesive composition.

27. The method of claim 24, wherein the anti-fungal agent is applied and is selected from the group consisting of parabens, cresols, and non-polymer-stabilized compounds.

28. The method of claim 24, wherein the anti-fungal agent is applied and is selected from the group consisting of alkyl parabens having an alkyl group of from 1–4 carbon atoms.

29. The method of claim 24, wherein the anti-fungal agent is applied and is selected from the group consisting of methylparaben, methylparaben sodium, ethylparaben, propylparaben, propylparaben sodium, butylparaben, cresol, chlorocresol, voriconazole, ketoconazole, fluconazole, itraconazole, miconazole, clotrimazole, saperconazole, neticonazole, oxiconazole, isoconazole, sulcopazole, tercanazole, tioconazole, naftifine, SF86-327, nyastatin, amphotericin B, pimaricin, benzoic acid and salts thereof, sorbic acid and salts thereof, propionic acids and salts thereof, boric acid and salts thereof, dehydroacetic acid, sulphurous and vanillic acids, alkyl esters of pararhydrobenzoic acid, thimerosal, phenylmercuric borate, phenylmercuric acetate and phenylmercuric nitrate, nitromersol, sodium ethylmercurithiosalicylate, benzalkonium chloride, benzethonium chloride, benzyl alcohol, cetylpyridinium chloride, chiorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, chlorothymol, alcohols, chlorobutanol, phenoxy-2-ethanol, benzyl alcohol, β-phenylethyl alcohol, chlorhexidine, 6-acetoxy-2,4-dimethyl-m-dioxane 2,4,4' trichloro-2'-hydroxy-diphenylether, imidizoldinylether urea compound, bromo-2-nitropropanediol-1,3 5-bromo-5-nitrol-1,3 dioxane, 2-methyl 1-4-isothiazolin-3-one and 5 chloro derivative, 1-(3-chloroallyl)-3,5,7-triazo 1-azoniaadamantane chloride and formaldehyde, imidazolidinyl urea, morpholines, salicylic acids, sodium iodides, potassium iodides, flucytosine, 5-flucytosine, griseofulvin, terbinafine, cidofovir, famicoclovir, valacyclovir, echinocandins, pneumocandins, pradimicins, benanomicins, nikkomycins, amorolfine, polyoxins, duanorubicin citrate, doxorubicin hydrocholride, tolnaftate, ciclopirox, butenafine, ergestrol biosynthesis inhibitors, acrisorein, 3-amino-4-hydroxybutyric acid, ammonium mercuric chloride, amorolfine, anthralin, azaserine, bifonazole, biphenamine, bromosalicylchloranilide, buclosamide, butoconazole, calcium propionate, candicidin, chlordantoin, chlormidazole, chlorphenesin, chlorquinaldol, cloconazole, cloxyquin, coparaffinate, m-cresyl acetate, cupric sulfate, dermostatin, diamthazole dihydrochloride, econazole, enilconazole, etisazol, exalamide, fenticonazole, filipin, flutrimazole, fungichromin, hachimycin, halethazole, hamycin, hexetidine, lanoconazole, loflucarban, lucensomycin, Magenta I, mepartricin, 2-(methoxymethyl)-5-nitrofuran, monensin, myxin, natamycin, neomycin undecylenate, nifuratel, oligomycins, omoconazole, ontianil, pecilocin, perimycin, pyrithione, pyrrolnitrin, rubijervine, salicylanilide, sertaconzole, siccanin, sulbentine, tenonitrozole, tolciclate, tolindate, triacetin, 2,4,6-tribromo-m-cresol, tubercidin, ujothion, undecylenic viridin, and zinc propionate.

30. The method of claim 30, wherein the anti-fungal agent is applied and is selected from the group consisting of elemental metals and metal compounds.

31. The method of claim 24, wherein the anti-fungal agent is applied and further comprises at least one of a diluent and a carrier.

32. The method of claim 24, wherein the anti-fungal agent is applied and is in the form of a liquid, a solid, a powder, or a cream.

33. The method of claim 24, wherein the skin care additive is applied and is selected from the group consisting of miconazole nitrate, povidone iodine complex, cliquinol, haloprogin, tolnaftate and undecylenic acid and mixtures thereof.

34. The method of claim 1, wherein said adhesive composition is applied directly to said area of skin, and said adhesive composition does not include an anti-fungal agent or a skin care additive.

35. The method of claim 34, wherein said polymer film has anti-fungal effects at said area of skin.

36. The method of claim 1, wherein said area of skin is selected from the group consisting of around skin folds, in a groin area, in a buttock area, on a trunk, under a breasts, and in an arm pit.

* * * * *